United States Patent
Xu et al.

(10) Patent No.: US 12,071,185 B2
(45) Date of Patent: Aug. 27, 2024

(54) SYSTEM AND METHOD FOR IDENTIFYING ADVERSE GEOLOGICAL BODY IN TUNNEL BASED ON HYPERSPECTRAL TECHNOLOGY ANALYSIS

(71) Applicant: SHANDONG UNIVERSITY, Shandong (CN)

(72) Inventors: Zhenhao Xu, Jinan (CN); Peng Lin, Jinan (CN); Tengfei Yu, Jinan (CN); Huihui Xie, Jinan (CN); Ruiqi Shao, Jinan (CN); Dongdong Pan, Jinan (CN); Fumin Liu, Jinan (CN); Gang Liu, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 233 days.

(21) Appl. No.: 17/618,745

(22) PCT Filed: Dec. 30, 2020

(86) PCT No.: PCT/CN2020/141568
§ 371 (c)(1),
(2) Date: Dec. 13, 2021

(87) PCT Pub. No.: WO2021/147639
PCT Pub. Date: Jul. 29, 2021

(65) Prior Publication Data
US 2022/0355876 A1    Nov. 10, 2022

(30) Foreign Application Priority Data
Jan. 21, 2020    (CN) .......................... 202010070787.4

(51) Int. Cl.
*G01N 21/31* (2006.01)
*B62D 57/024* (2006.01)
(Continued)

(52) U.S. Cl.
CPC ........... *B62D 57/024* (2013.01); *B62D 57/04* (2013.01); *E21D 9/003* (2013.01); *G01N 21/31* (2013.01); *G01N 33/24* (2013.01)

(58) Field of Classification Search
CPC ...... B62D 57/024; B62D 57/04; E21D 9/003; G01N 21/31; G01N 33/24
See application file for complete search history.

(56) References Cited

U.S. PATENT DOCUMENTS 6,160,618 A * 12/2000 Garner ............... G01N 21/6456
250/461.1
6,422,508 B1 * 7/2002 Barnes ...................... G01J 3/06
342/63

(Continued)

FOREIGN PATENT DOCUMENTS

| CN | 103175801 A | 6/2013 |
| CN | 103308454 A | 9/2013 |

(Continued)

OTHER PUBLICATIONS

Chakravorty, Adityarup. Underground Robots: How Robotics is Changing the Mining Industry, May 13, 2019 [retrieved on Feb. 22, 2024]. Retrieved from the internet < URL: http: eos.org/underground-robots-how-robotics-is-changing-the-mining-industry> (Year: 2019).*

(Continued)

*Primary Examiner* — Rina I Duda
(74) *Attorney, Agent, or Firm* — Oliff PLC

(57) ABSTRACT

A system and a method identify an adverse geological body in a tunnel based on hyperspectral technology analysis. The system includes a wall-climbing robot, a controller, and a signal processor, wherein the wall-climbing robot is provided with a plurality of groups of hyperspectral light sources and receivers, and the hyperspectral light sources and the receivers are arranged at intervals; the controller is configured to control the operation of the wall-climbing (Continued)

robot to ensure that the wall-climbing robot moves on a tunnel face according to a set spiral path; and the signal processor communicates with the receivers to receive the acquired spectrum data, draws a mineral distribution map of the tunnel face with the path raveled by the wall-climbing robot as a plane, and identifies an adverse geological body by identifying categories and distribution characteristics of the representative minerals.

7 Claims, 4 Drawing Sheets

(51) Int. Cl.
*B62D 57/04* (2006.01)
*E21D 9/00* (2006.01)
*G01N 33/24* (2006.01)

(56) References Cited

U.S. PATENT DOCUMENTS

| | | | | |
|---|---|---|---|---|
| 6,481,513 B2 * | 11/2002 | Buehler | ................ | B62D 63/02 |
| | | | | 901/1 |
| 7,069,124 B1 * | 6/2006 | Whittaker | ............ | G05D 1/0274 |
| | | | | 701/28 |
| 7,415,321 B2 * | 8/2008 | Okazaki | ................ | B25J 9/1697 |
| | | | | 901/1 |
| 8,392,036 B2 * | 3/2013 | Jacobsen | .............. | G05D 1/0044 |
| | | | | 701/2 |
| 8,743,358 B2 * | 6/2014 | Treado | ................... | G01N 21/65 |
| | | | | 356/326 |
| 8,793,106 B2 * | 7/2014 | Baseman | ......... | G05B 19/41875 |
| | | | | 703/2 |
| 8,835,015 B2 * | 9/2014 | Su | ........................... | B32B 27/32 |
| | | | | 428/910 |
| 9,586,636 B1 * | 3/2017 | Burmeister | .......... | B62D 53/028 |

FOREIGN PATENT DOCUMENTS

| | | |
|---|---|---|
| CN | 103699889 A | 4/2014 |
| CN | 108447572 A | 8/2018 |
| CN | 108731736 A | 11/2018 |
| CN | 108896739 A | 11/2018 |
| CN | 109375275 A | 2/2019 |
| CN | 109564952 A | 4/2019 |
| CN | 208766123 U | 4/2019 |
| CN | 109959624 A | 7/2019 |
| CN | 110031491 A | 7/2019 |
| CN | 111267984 A | 6/2020 |
| JP | 2019-039913 A | 3/2019 |
| WO | 2019/191497 A1 | 10/2019 |

OTHER PUBLICATIONS

Apr. 6, 2021 Search Report issued in International Patent Application No. PCT/CN2020/141568.
Apr. 7, 2021 Written Opinion issued in International Patent Application No. PCT/CN2020/141568.
Nov. 2, 2020 Office Action issued in Chinese Patent Application No. 202010070787.4.

* cited by examiner

SYSTEM AND METHOD FOR IDENTIFYING ADVERSE GEOLOGICAL BODY IN TUNNEL BASED ON HYPERSPECTRAL TECHNOLOGY ANALYSIS

FIELD OF THE INVENTION

The present disclosure belongs to the technical field of identification of an adverse geological body and specifically relates to a system and a method for identifying an adverse geological body in a tunnel based on hyperspectral technology analysis.

BACKGROUND OF THE INVENTION

The statement of this section merely provides background art information related to the present disclosure and does not necessarily constitute the prior art.

During tunnel construction, an adverse geological body very easily induces large-scale and sudden water and mud inrush disasters, causing many problems such as casualties, construction delays, and equipment damage. Identifying an adverse geological body is an important task of tunneling. Common adverse geological bodies are mainly faults, fracture zones, alteration zones, etc. Faults and fracture zones are often accompanied by some clay minerals, such as kaolinite, illite, and chlorite. These minerals are mainly distributed in fault zones, while are less or even not developed in surrounding rock on two sides along the fault zones. In the alteration zones, due to the intrusion of underground hydrothermal fluid, the rock in strata is altered to form new minerals, such as garnet and ophiolite, and these minerals only exist in the altered zones or the surrounding rock near the altered zones. According to the distribution law of the representative minerals for an adverse geological body, the adverse geological body can be identified.

However, as far as the inventors know, the identification of the adverse geological body in a tunnel based on hyperspectral technology analysis mainly depends on the naked eye, and there are some uncertain factors in the identification by the naked eye, for example, chlorite and epidote have similar characteristics and are easily confused; and kaolinite, anorthose and calcite have similar problems such as non-obvious boundary, which have certain interference in the identification and judgment of the adverse geological body. To determine the exact boundary, laboratory analysis is required. The laboratory analysis has high accuracy but has a long cycle, wastes time, and prolongs the construction period.

SUMMARY OF THE INVENTION

To solve the above problems, the present disclosure proposes a system and a method for identifying an adverse geological body in a tunnel based on hyperspectral technology analysis, which is simple in operation and fast in identification speed and can achieve qualitative identification of minerals in the adverse geological body.

According to some embodiments, the present disclosure adopts the following technical solutions:

A system for identifying an adverse geological body in a tunnel based on hyperspectral technology analysis, including a wall-climbing robot, a controller, and a signal processor, wherein the wall-climbing robot is provided with a plurality of groups of hyperspectral light sources and receivers, and the hyperspectral light sources and the receivers are arranged at intervals;

the controller is configured to control the operation of the wall-climbing robot to ensure that the wall-climbing robot moves on a tunnel face according to a set spiral path;

the signal processor communicates with the receivers to receive the acquired spectrum data, draws a mineral distribution map of the tunnel face with the path traveled by the wall-climbing robot as a plane, and identifies an adverse geological body by identifying categories and distribution characteristics of the representative minerals.

As a further limitation, the wall-climbing robot includes a robot body, a holder is arranged at an upper part of the robot body, a camera is arranged on the holder, a middle part of the robot body is equipped with a spiral thrust system, spiral thrust devices are respectively arranged on sides and a top of the spiral thrust system, the top spiral thrust enables the robot body to fit an inner wall of the tunnel, the lateral spiral thrusts balance the robot and enable the robot to move along a curve at the same time, a bottom of the robot body is equipped with the hyperspectral light sources and receivers, the hyperspectral light sources and the receivers are arranged at intervals, and a plurality of supporting force telescopic rods are arranged at a lower end of the robot body.

As a further limitation, the spiral thrust devices are respectively arranged on the sides of the spiral thrust system in different directions.

As a further limitation, the signal processor is configured to receive mineral reflection spectrum information, compare the spectrum information with database standard spectra, calculate correlations of corresponding peaks and troughs, determine mineral names according to the correlations, draw a mineral distribution map of the tunnel face, and then identify whether the mineral categories and mineral distribution characteristics in the mineral distribution map are of an adverse geological body.

As a further limitation, when the wall-climbing robot moves on the tunnel face, the route is spiral, and the wall-climbing robot moves toward the center of the tunnel face spirally cycle by cycle along the edge of the tunnel face.

As a further limitation, the wall-climbing robot crawls from a sidewall of the tunnel to the tunnel face through the supporting force telescopic rods at the bottom of the robot body and the spiral thrust system, and the supporting force telescopic rods can rotate in any direction about their portions in contact with the robot body as endpoints.

As a further limitation, lamps are further arranged on the holder, and the camera cooperates with the lamps.

As a further limitation, crawlers are arranged on two sides of the robot body to prevent the uneven tunnel face from obstructing the advancement of the wall-climbing robot.

As a further limitation, the sides and top of the spiral thrust system are respectively equipped with spiral thrust devices, each spiral blade of the lateral spiral thrust devices can work independently to balance the gravity of the wall-climbing robot using reverse thrust, and the reverse thrust of top spiral blades ensures that the wall-climbing robot can move stably on the tunnel face.

A working method based on the above system includes the following steps:

placing the wall-climbing robot on a tunnel plane, and controlling the wall-climbing robot to move; when the wall-climbing robot moves to a tunnel face, controlling the corresponding supporting force telescopic rods of the wall-climbing robot to extend, controlling the magnitude of thrust generated by the spiral thrust system in each direction so that the wall-climbing robot reaches a state of moving at a constant speed, and turning on the hyperspectral light sources and the spectral receivers at the same time;

traveling a spiral path set in advance;

during the movement of the wall-climbing robot, the hyperspectral light sources and the spectral receivers start to work and transmit the collected information at the same time, and the signal processor receives mineral reflection spectrum information, then drawing the reflection spectrum information into a spectrum curve graph and comparing the same with database standard mineral spectrum curves;

comparing peaks and troughs information in the collected spectrum information with peaks and troughs of the database standard mineral spectrum curves by using a peak-trough correlation coefficient method, calculating correlations between them, and selecting the database standard mineral curve with the highest correlation of peaks and troughs, thus obtaining mineral names, i.e. test minerals; and drawing a mineral distribution map of the tunnel face based on the path traveled by the wall-climbing robot and the corresponding mineral name corresponding to each point; determining whether an adverse geological body exists based on distribution characteristics of representative minerals for the adverse geological body in the drawn mineral distribution map.

As a further limitation, the spiral path is set based on the area of the tunnel face and thrust angles and the number of thrusts of the lateral spiral thrust devices of the wall-climbing robot, and the changing of magnitudes of the thrusts is set based on the moving speed of the wall-climbing robot and time.

Compared with the prior art, the beneficial effects of the present disclosure are:

The wall-climbing robot collects mineral reflection spectrum information, and the computer processes the data, which can accurately point out locations of various minerals on the tunnel face and catalog the minerals on the tunnel face, thereby realizing the fast identification of minerals on the tunnel face and the fast identification of the adverse geological body. Compared with the current identification of the adverse geological body in a tunnel, the identification accuracy of the adverse geological body is improved, and the speed of identifying minerals on the tunnel face is improved by using spectral technology and computer data processing means.

BRIEF DESCRIPTION OF THE DRAWINGS

The accompanying drawings constituting a part of the present disclosure are used for providing a further understanding of the present disclosure, and the schematic embodiments of the present disclosure and the descriptions thereof are used for interpreting the present disclosure, rather than constituting improper limitations to the present disclosure.

Figure 1:
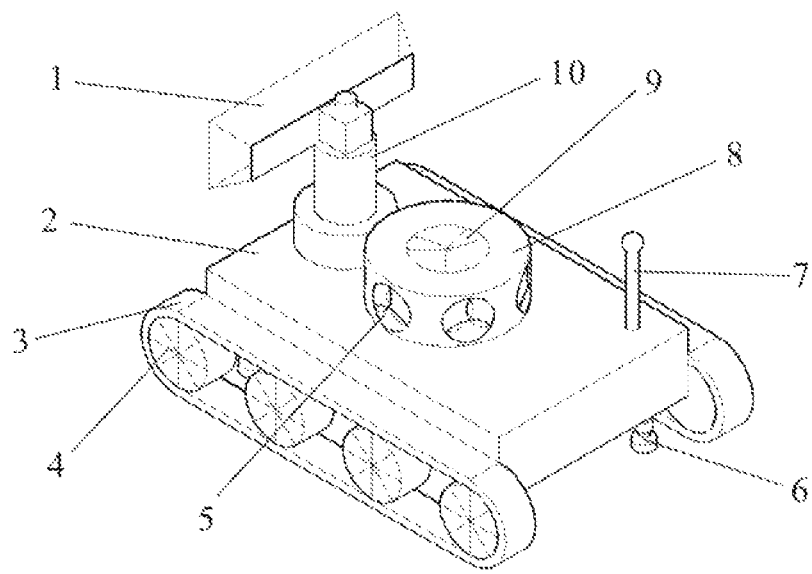
FIG. 1 is an overall view of a wall-climbing robot.

In the figures, 1—lens; 2—main board box; 3—crawler; 4—wheel; 5—spiral lateral thrust device; 6—supporting telescopic rod; 7—antenna (electromagnetic wave receiver/transmitter); 8—spiral thrust system; 9—top spiral thrust device; 10—holder; 11—lamp; 12—spectrum emitter/receiver; 13—tunnel face; 14—tunnel horizontal plane; 15—wall-climbing robot; 16—tunnel face spiral path; F1—top spiral thrust; F2—lateral spiral thrust (to balance the gravity of the wall-climbing robot); F3—lateral spiral thrust (to help the wall-climbing robot to turn around).

DETAILED DESCRIPTION OF EMBODIMENTS

The present disclosure will be further illustrated below in conjunction with the accompanying drawings and embodiments.

It should be noted that the following detailed descriptions are exemplary and are intended to provide further descriptions of the present disclosure. All technical and scientific terms used herein have the same meaning as commonly understood by those of ordinary skill in the technical field to which the present disclosure belongs unless otherwise indicated.

It should be noted that the terms used here are merely used for describing specific embodiments, but are not intended to limit the exemplary embodiments of the present disclosure. As used herein, unless otherwise clearly stated in the context, the singular form is also intended to include the plural form. In addition, it should also be understood that when the terms "include" and/or "comprise" are used in the Description, they indicate features, steps, operations, devices, components, and/or combinations thereof.

In the present disclosure, the terms such as "upper", "lower", "left", "right", "front", "rear", "vertical", "horizontal", "side", and "bottom" indicate the orientation or positional relationships based on the orientation or positional relationships shown in the drawings, are only relationship terms determined for the convenience of describing the structural relationships of various components or elements of the present disclosure, but do not specify any component or element in the present disclosure, and cannot be understood as limitations to the present disclosure.

In the present disclosure, the terms such as "fixed", "connected" and "coupled" should be generally understood, for example, they may be fixedly connected, detachably connected, integrally connected, directly connected, or indirectly connected by a medium. For a related scientific researcher or a technical person in this art, the specific meanings of the above terms in the present disclosure may be determined according to specific circumstances, and cannot be understood as limitations to the present disclosure.

A device for identifying an adverse geological body in a tunnel based on hyperspectral technology analysis includes three systems of an information acquisition system, a data processing system, and a signal identification system.

Wherein, the information acquisition system includes a wall-climbing robot, light source emission, spectrum reception, and information transmission. The information acquisition system is realized by the wall-climbing robot and a computer together.

Figure 2:
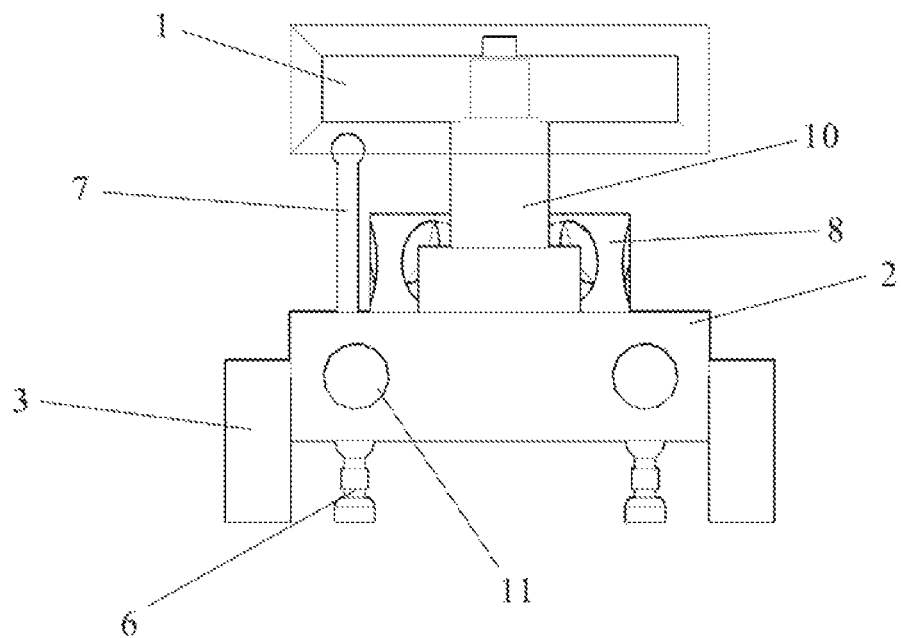
FIG. 2 is a left view of the wall-climbing robot.

As shown in FIG. 1 and FIG. 2, the wall-climbing robot includes a cuboid mainboard box, the mainboard box is used for placing a wall-climbing robot controller and a power device, and the wall-climbing robot completes instructions through the controller; crawlers are mounted on two sides of the mainboard box, and wheels are mounted inside the crawlers, and such configuration is used to prevent difficult advancement of the wall-climbing robot due to unevenness of a tunnel face, and two lamps are mounted in the front of the mainboard box.

A holder is arranged in the front of the upper part of the mainboard box, a prism frustum-shaped lens is arranged on the holder, and the combination of the lamps and the holder can be used to detect specific statuses of minerals and rock on the tunnel face; a middle part of the mainboard box is equipped with a cylindrical spiral thrust system, spiral thrust devices are respectively arranged on sides and a top of the spiral thrust system, the top spiral thrust ensures stable contact between the wall-climbing robot and the tunnel face, and the side thrust devices are used to balance the gravity of the wall-climbing robot and control the wall-climbing robot to change its movement path.

Figure 3:
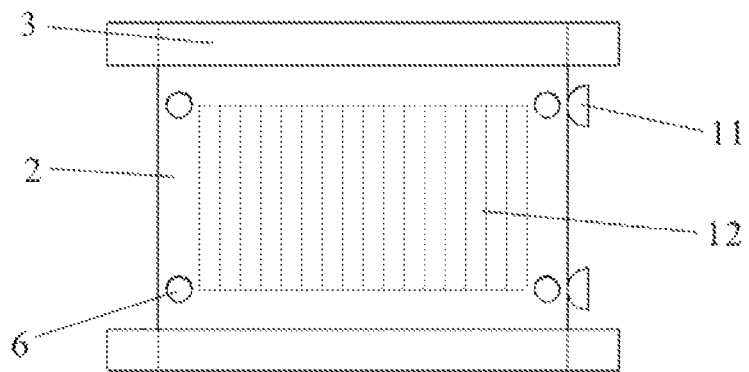
FIG. 3 is a bottom view of the wall-climbing robot.

An antenna is mounted on the right of the back of the mainboard box, and the antenna is used to communicate with the computer for data transmission and command reception; a bottom of the main board box is equipped with a rectangular hyperspectral light source and receiver system, light sources and receivers are staggered, and this part is used to collect mineral reflection spectra; as shown in FIG. 3, supporting force telescopic rods are respectively arranged at four corners of the rectangular hyperspectral system, and the supporting force telescopic rods are used to assist the wall-climbing robot is changing the working face, for example, the changing from the tunnel wall to the tunnel face.

Both the data processing system and the signal identification system are implemented by the computer. After receiving mineral reflection spectrum information, the computer immediately processes data, compares the spectrum information with database standard spectra, calculates correlations of corresponding peaks and troughs, determines mineral names according to the correlations, and draws a mineral distribution map of the tunnel face; and after the data processing, the signal identification system identifies whether the mineral categories and mineral distribution characteristics in the mineral distribution map are of an adverse geological body.

Figure 4:
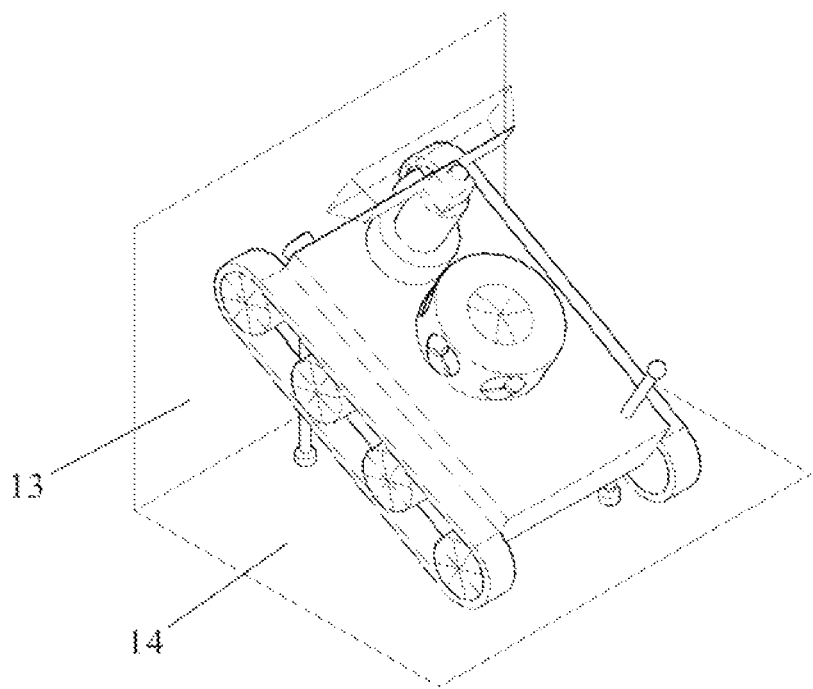
FIG. 4 is a diagram of the wall-climbing robot climbing a wall.
Figure 5:
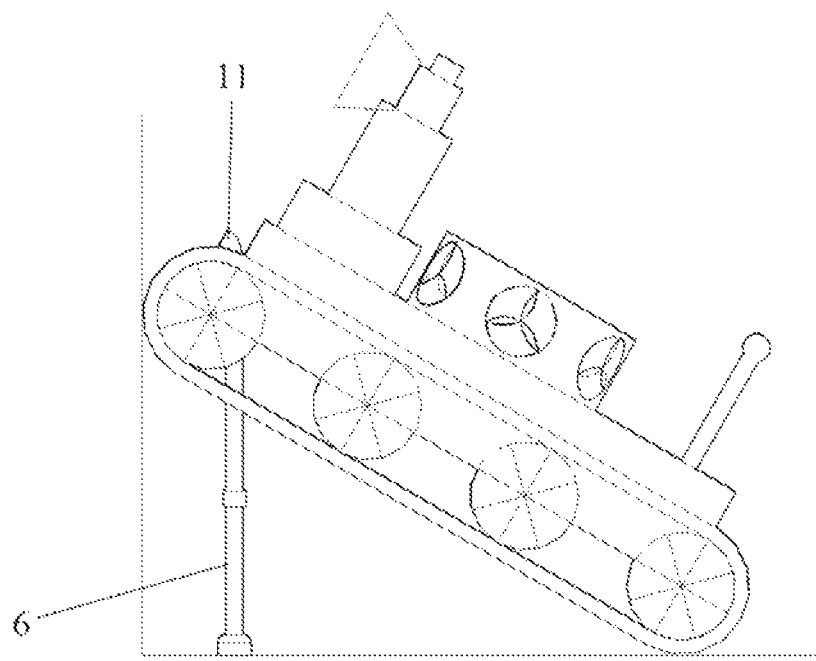
FIG. 5 is a front view of the wall-climbing robot climbing the wall.
Figure 6:
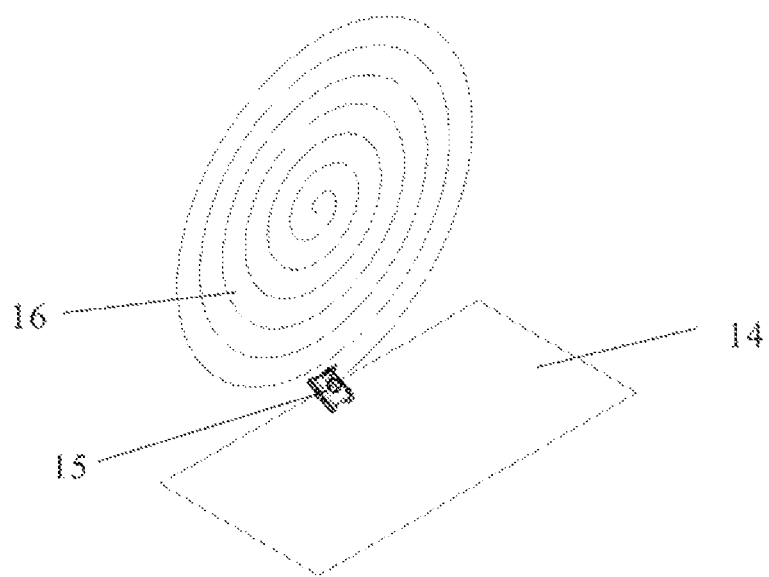
FIG. 6 shows a spiral path between the wall-climbing robot and a tunnel face.
Figure 7:
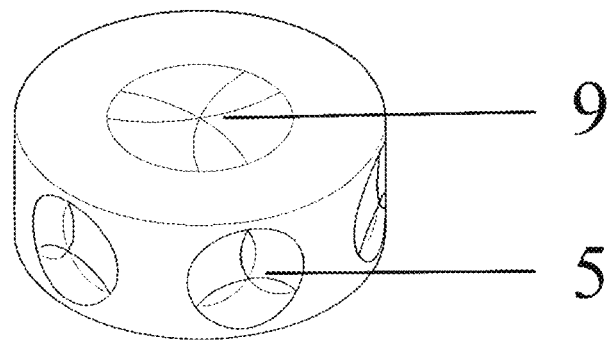
FIG. 7 shows a spiral thrust system.
Figure 8:
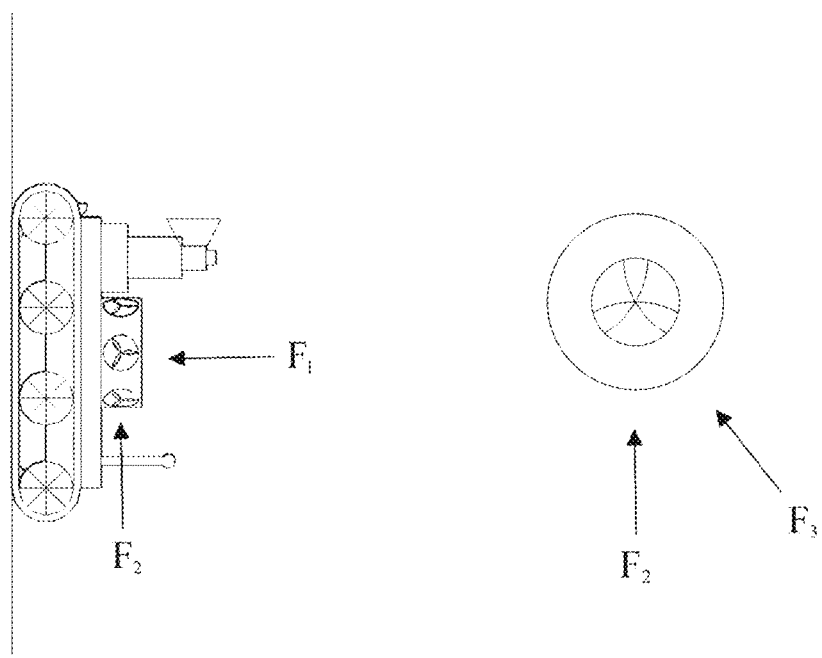
FIG. 8 is a force diagram of the wall-climbing robot on the wall.

The identification of an adverse geological body by using the above-mentioned device includes the following steps:

1) The wall-climbing robot is placed on a tunnel plane and controlled by the computer to move; when the wall-climbing robot moves to a tunnel face, two supporting force telescopic rods in the front of the wall-climbing robot are controlled by the computer to extend, as shown in FIGS. 4 and 5, and the reverse spiral thrust device in the spiral thrust system is turned on;
2) As the wall-climbing robot slowly climbs the wall, the thrust of the spiral thrust device gradually increases; when the wall-climbing robot is in a vertical state, that is, parallel to the tunnel face, the lateral spiral thrust is greater than the gravity, the top thrust is applied at the same time, the wall-climbing robot reaches a uniform movement state, and the hyperspectral light sources and the spectral receivers are turned on at the same time;
3) A spiral path set in the computer in advance is s1elected, and a spiral path instruction is sent to the wall-climbing robot. As shown in FIG. 6, the spiral path is set based on the area of the tunnel face and thrust angles and the number of thrusts of the lateral spiral thrust devices of the wall-climbing robot, and the changing of magnitudes of the thrusts is set based on the moving speed of the wall-climbing robot and time;
4) During the movement of the wall-climbing robot, the hyperspectral light sources and the spectral receivers start to work, and transmit the collected information to the computer through the antenna; after receiving mineral reflection spectrum information, the computer draws the reflection spectrum information into a spectrum curve graph and compares the same with database standard mineral spectrum curves;
5) Peaks and troughs information in the collected spectrum information are compared with peaks and troughs of the database standard mineral spectrum curves by using a peak-trough correlation coefficient method, and correlations therebetween are calculated; when the correlation is closer to 1, the collected minerals are highly similar to database standard minerals; the database standard mineral curve with the highest correlation of peaks and troughs is selected, and mineral names, i.e. test minerals, are obtained;
6) A mineral distribution map of the tunnel face is drawn based on the path traveled by the wall-climbing robot and the corresponding mineral name corresponding to each point; whether an adverse geological body exists is determined based on distribution characteristics of the representative minerals for the adverse geological body in the drawn mineral distribution map;
7) When the wall-climbing robot completes the set route, the computer draws the required mineral distribution map of the tunnel face and carries out the identification, which is considered as the completion of the identification.

Described above are merely preferred embodiments of the present disclosure, and the present disclosure is not limited thereto. Various modifications and variations may be made to the present disclosure for those skilled in the art. Any modification, equivalent substitution, improvement, or the like made within the spirit and principle of the present disclosure shall fall into the protection scope of the present disclosure.

Although the specific embodiments of the present disclosure are described above in combination with the accompanying drawing, the protection scope of the present disclosure is not limited thereto. It should be understood by those skilled in the art that various modifications or variations could be made by those skilled in the art based on the technical solution of the present disclosure without any creative effort, and these modifications or variations shall fall into the protection scope of the present disclosure.

The invention claimed is:

1. A system for identifying an adverse geological body in a tunnel based on hyperspectral technology analysis, comprising a wall-climbing robot, a controller, and a signal processor, wherein:

the wall-climbing robot comprises a robot body, a middle part of the robot body is equipped with a spiral thrust system, spiral thrust devices are respectively arranged on sides and a top of the spiral thrust system, and each spiral blade of the spiral thrust devices on sides of the spiral thrust system can work independently, wherein reverse thrusts of lateral spiral thrust devices balance gravity of the wall-climbing robot, and can ensure that the robot advances along a curve, and a reverse thrust of spiral blades on the top of the spiral thrust system enables the wall-climbing robot to fit an inner wall of the tunnel;

a bottom of the robot body is provided with a plurality of groups of hyperspectral light sources and receivers, and the hyperspectral light sources and the receivers are arranged at intervals;

a holder is arranged at an upper part of the robot body, a camera is arranged on the holder; and a plurality of supporting force telescopic rods are arranged at a lower end of the robot body;

the controller is configured to control an operation of the wall-climbing robot to ensure that the wall-climbing robot moves on a tunnel face according to a set spiral path, wherein, when the wall-climbing robot moves on the tunnel face, a route of the wall-climbing robot is spiral, and the wall-climbing robot moves toward a center of the tunnel face spirally cycle by cycle along an edge of the tunnel face; and the signal processor is configured to communicate with the receivers to receive the acquired spectrum data, draw a mineral distribution map of the tunnel face with the path traveled by the wall-climbing robot as a plane, and identify an adverse geological body by identifying categories and distribution characteristics of representative minerals.

2. The system for identifying an adverse geological body in a tunnel based on hyperspectral technology analysis according to claim 1, wherein the signal processor is configured to receive mineral reflection spectrum information, compare the spectrum information with database standard spectra, calculate correlations of corresponding peaks and troughs, determine mineral names according to the correlations, draw a mineral distribution map of the tunnel face, and then identify whether mineral categories and mineral distribution characteristics in the mineral distribution map are of an adverse geological body.

3. The system for identifying an adverse geological body in a tunnel based on hyperspectral technology analysis according to claim 1, wherein the wall-climbing robot is configured to crawl from a sidewall of the tunnel to the tunnel face through the supporting force telescopic rods at the bottom of the robot body and the spiral thrust system at the top of the robot body, and the supporting force telescopic rods can rotate in any direction about their portions in contact with the robot body as endpoints.

4. The system for identifying an adverse geological body in a tunnel based on hyperspectral technology analysis according to claim 1 wherein lamps are further arranged on the holder, and the camera cooperates with the lamps.

5. The system for identifying an adverse geological body in a tunnel based on hyperspectral technology analysis according to claim 1, wherein crawlers are arranged on two sides of the robot body to prevent an uneven tunnel face from obstructing the advancement of the wall-climbing robot.

6. A working method based on the system according to claim 1, comprising the following steps:

placing the wall-climbing robot on a tunnel plane, and controlling the wall-climbing robot to move; when the wall-climbing robot moves to a tunnel face, controlling the corresponding supporting force telescopic rods of the wall-climbing robot to extend, controlling a magnitude of thrust generated by the spiral thrust system in each direction so that the wall-climbing robot reaches a state of moving at a constant speed, and turning on the hyperspectral light sources and the spectral receivers at the same time;

traveling a spiral path set in advance;

during a movement of the wall-climbing robot, the hyperspectral light sources and the spectral receivers start to work and transmit the collected information at the same time, and the signal processor receives mineral reflection spectrum information, then drawing the reflection spectrum information into a spectrum curve graph and comparing the same with database standard mineral spectrum curves;

comparing peaks and troughs information in the collected spectrum information with peaks and troughs of the database standard mineral spectrum curves by using a peak-trough correlation coefficient method, calculating correlations between them, and selecting the database standard mineral curve with the highest correlation of peaks and troughs, thus obtaining mineral names; and drawing a mineral distribution map of the tunnel face based on the path traveled by the wall-climbing robot and the corresponding mineral name corresponding to each point; determining whether an adverse geological body exists based on distribution characteristics of the representative minerals for the adverse geological body in the drawn mineral distribution map.

7. The working method according to claim 6, wherein the spiral path is set based on an area of the tunnel face and thrust angles and a number of thrusts of the lateral spiral thrust devices of the wall-climbing robot, and magnitudes of the thrusts is set based on the moving speed of the wall-climbing robot and time.

* * * * *